United States Patent
Bright et al.

(10) Patent No.: US 7,759,522 B2
(45) Date of Patent: Jul. 20, 2010

(54) PROCESS FOR PURIFICATION OF PHOSPHATE ESTERS

(75) Inventors: Danielle A. Bright, New City, NY (US); Eric W. Burkhardt, Brewster, NY (US); Antoon ten Kate, Arnhem (NL); Sophia Dashevsky, Monroe Township, NJ (US); John Tomko, Dobbs Ferry, NY (US)

(73) Assignee: Supresta LLC, Ardsley, NY (US)

( * ) Notice: Subject to any disclaimer, the term of this patent is extended or adjusted under 35 U.S.C. 154(b) by 1123 days.

(21) Appl. No.: 10/467,262

(22) PCT Filed: Feb. 8, 2002

(86) PCT No.: PCT/US02/03522

§ 371 (c)(1),
(2), (4) Date: Jan. 16, 2004

(87) PCT Pub. No.: WO02/062808

PCT Pub. Date: Aug. 15, 2002

(65) Prior Publication Data

US 2004/0116728 A1    Jun. 17, 2004

Related U.S. Application Data

(60) Provisional application No. 60/267,259, filed on Feb. 8, 2001.

(51) Int. Cl.
*C07F 9/12* (2006.01)
(52) U.S. Cl. ........................................ 568/14
(58) Field of Classification Search ............ 568/14
See application file for complete search history.

(56) References Cited

U.S. PATENT DOCUMENTS

| 3,954,917 | A  | 5/1976 | Honig et al. |
| 4,205,023 | A  | 5/1980 | Anzenberger, Sr. |
| 5,616,768 | A  | 4/1997 | Kawata et al. |
| 6,706,907 | B1 | 3/2004 | Hirao et al. |

FOREIGN PATENT DOCUMENTS

| EP | 0496937 | | 9/1991 |
| EP | 0690063 | | 1/1996 |
| EP | 0909790 | | 10/1998 |
| EP | 0 909 790 | * | 4/1999 |
| EP | 2001/002945 | | 1/2001 |
| EP | 2001/131392 | | 5/2001 |
| EP | 1205483 | A1 | 5/2002 |
| FR | 2374354 | | 7/1978 |
| JP | 50151803 | | 12/1975 |
| JP | 8067685 | | 3/1996 |
| JP | 10310593 | | 11/1998 |
| JP | 2000239285 | | 9/2000 |
| WO | WO0112638 | | 2/2001 |

OTHER PUBLICATIONS esp@cenet Abstract of JP 2001-002945 Jan. 2001.

* cited by examiner

*Primary Examiner*—Rebecca L Anderson
(74) *Attorney, Agent, or Firm*—Dilworth & Barrese, LLP.

(57) ABSTRACT

A crude phosphate ester product can be purified by first washing it with chelating agent composition (such as a dilute acidic solution) and then, preferably, water, drying the resulting product, and then treating the resulting product with an acid scavenger, as exemplified by an epoxy-containing compound, such as 3,4-epoxy cyclohexyl methyl-3,4-epoxy cyclohexyl carboxylate.

6 Claims, No Drawings

PROCESS FOR PURIFICATION OF PHOSPHATE ESTERS

This application is a 371 of PCT/US02/03522, filed Feb. 8, 2002, and claims benefit of 60/267,259, filed Feb. 8, 2001.

The present invention is useful in the purification of phosphate ester compositions, in general, with aromatic oligomeric phosphate ester compositions being a preferred class of material for treatment.

For example, aromatic oligomeric phosphates, which are used as flame retardants for thermoplastic resins, are made by reaction of $POCl_3$ with a biphenol or a diol followed by reaction with phenol (or, alternatively, by reaction of diphenyl chlorophosphate with a biphenol) in the presence of a Lewis acid catalyst to form what is termed a "crude phosphate" composition. Usually, extensive washing of this type of product is needed to remove catalyst residues (for example, such metal species as magnesium, aluminum, zinc, and titanium) and other acidic impurities that may negatively impact the properties of polymers (for example, polycarbonates, polyesters, and the like) to which the flame retardant is to be added.

In Examples 1 to 6 of U.S. Pat. No. 5,616,768 to S. Kawata, such a reaction product is washed with an acidic aqueous solution to remove the catalyst and is then dried under reduced pressure. In Examples 1 to 14 of the same patent, the crude ester is treated with an epoxy compound at elevated temperature, washed with water, heated for a certain time and washed again with water. The oil layer is then dried under reduced pressure to give a purified product. This process is cumbersome and involves two wash and two drying sequences.

The present invention is a new, simplified purification process to obtain a product of low metal content and low acidity. This new process comprises washing the reaction product with a dilute solution of a chelating agent. As used herein, the term "chelating agent" is intended to encompass those molecules and ions that can bond to a metal cation. Examples suitable chelating agent compositions for use herein include dilute acidic aqueous solutions that comprise an Arhenius acid, such as hydrochloric acid, phosphoric acid, carboxylic acids, a phosphonic acid, sulfuric acids, sulfonic acids, and the like. Also solutions containing such chelating agent as ethylenediamine or ethylenediaminetetraacetic acid (EDTA) can also be employed. The process herein involves washing the crude reaction product with such a chelating agent, followed, preferably, by one or two water washes to remove the catalyst. The chelating agent is essential to effect the removal of Lewis acid catalyst residues (see Comparative Example 1). The chelating agent treatment preferably takes place at temperatures that range from about 40° C. to about 90° C. using an amount of chelating agent, on an active basis, that ranges from about equimolar to about 100% over equimolar. The use of temperatures near the upper limit of the aforementioned temperature range will result in a shorter time within which the desired reaction of chelating agent and metal occurs.

The use of the preferred water washes following the dilute chelating agent wash allow for removal of excess chelating agent from the phosphate ester oil, thereby contributing to a decrease in acidity (see, for example, Example 2, which follows).

The crude product is then preferably dried under reduced pressure, filtered and is then treated with an acid scavenger. Drying of the crude product prior to treatment with the acid scavenger is also important to the process of this invention since the presence of water impedes the action of the acid scavenger additive (see, for example, Example 9, which follows).

Useful, representative acid scavengers are compounds containing epoxy groups. Examples of suitable epoxy compounds that can be used in accordance with the present invention include ethylene oxide, propylene oxide, cyclohexene oxide, styrene oxide, epoxidized soybean oil, 3,4-epoxycyclohexyl-methyl-3,4-epoxy-cyclohexane-carboxylate, vinyl cyclohexene dioxide, 2-(3,4-epoxycyclohexyl-5,5-spiro-3,4-epoxy)cyclohexane-meta-dioxane, bis(3,4-epoxycyclohexyl)adipate, 1,2-epoxy-p-vinylcyclohexene, Bisphenol A epoxy resins (for example, ARALDITE®, a brand name of Ciba Specialty Chemicals), and the like. In general, it is preferred that the number of equivalents of epoxy used be equal to or greater than the number of equivalents of acid present in the crude phosphate ester based on the Total Acid Number ("TAN") of the crude phosphate ester. Total Acid Number is defined as the number of milligrams of potassium hydroxide required to neutralize one gram of sample, the determination of which is described in ASTM method D974. The treatment with the acid scavenger can take place at temperatures that can range from about 25° C. to about 200° C. The amount of acid scavenger that is employed, on an actives basis, can generally range from about stoichiometric amount to about 100% excess, based on the acid number.

The Examples that follow illustrate this invention.

EXAMPLE 1

Synthesis of Reaction Mixture

To 1249.2 g. of "DPCP mix" (this mixture contains mainly diphenyl chlorophosphate, "DPCP", and small amounts of monophenyl dichlorophosphate and triphenyl phosphate) and 4.2 g. of magnesium chloride, which was heated to 140° C. under 50 mm vacuum, was continuously added 513 g. of bisphenol A over an eight hour period. At the end of this addition, the reaction mixture was held at 140° C. for an additional three and one half-hours. The resulting crude phosphate ester had an acid number of 4.4 mg. KOH/g. The magnesium content of the crude product was 2600 ppm.

EXAMPLE 2

Purification of Reaction Mixture

Step 1: To 1200 g. of 0.4% oxalic acid in water, which was heated to 90° C. with stirring, was added 1000 g. of the reaction mixture from Example 1. The mixture was agitated for thirty minutes and was allowed to separate. The acid number of the oil was 0.74 mg. KOH/g. The oil layer was washed twice with water at 65° C. and was dried under vacuum to give 913.2 g. of product. The magnesium content of this product was 20 ppm, and the acid number was 0.48 mg. KOH/g.

Step 2: To the oil from step 1 of this Example (acid number=0.48 mg. KOH/g) was added, with stirring at 65° C., 1.39 g. of 3,4-epoxy cyclohexyl methyl-3,4-epoxy cyclohexyl carboxylate, "ERL 4221" brand (a bis epoxide product available from Union Carbide). After four hours, the acid number of the resulting Bisphenol A bis(diphenyl phosphate) product, "BDP", was 0.019 mg. KOH/g.

Examples 3 to 5, which follow, show alternative embodiments for practicing just step 1 of the purification of the reaction mixture that was previously exemplified.

EXAMPLE 3

Purification of Reaction Mixture

Step 1: To 600.3 g. of 1% phosphoric acid in water, which was heated to 90° C. with stirring, was added 503.8 g. of the reaction mixture from Example 1. The mixture was agitated for ninety minutes and was allowed to separate. The acid number of the oil was 0.45 mg. KOH/g. The oil layer was washed once with water at 65° C. and was dried under vacuum to give 512.0 g. of product. The magnesium content of this product was 38 ppm, and the acid number was 0.28 mg. KOH/g.

EXAMPLE 4

Purification of Reaction Mixture

Step 1: To 550 g. of 0.8% DEQUEST sequestrant 2010 (1-hydroxyethylidene-1-1-diphosphonic acid, from Solutia) in water, which was heated to 90° C. with stirring, was added 445.8 g. of the reaction mixture from Example 1. The mixture was agitated for ninety minutes and was allowed to separate. The acid number of the oil was 1.22 mg. KOH/g. The oil layer was washed once with water at 65° C. and was dried under vacuum to give 444.1 g. of product. The magnesium content of this product was 40 ppm, and the acid number was 0.29 mg. KOH/g.

EXAMPLE 5

Purification of Reaction Mixture

Step 1: To 605.5 g. of 0.9% BAYHIBIT AM (2-Phosphono-1,2,4-butane tricarboxylic acid, from Bayer) in water, which was heated to 90° C. with stirring, was added 504.7 g. of the reaction mixture from Example 1. The mixture was agitated for ninety minutes and was allowed to separate. The acid number of the oil was 0.28 mg. KOH/g. The oil layer was washed once with water at 65° C. and was dried under vacuum to give 504.7 g. of product. The magnesium content of this product was 11 ppm, and the acid number was 0.21 mg. KOH/g.

Examples 6-8, which follow, show alternative embodiments for practicing just step 2 of the purification of the reaction mixture.

EXAMPLE 6

Purification of Reaction Mixture

Step 2: To 1216 g. of crude BDP that was previously washed with oxalic acid and water as described in step 1 of Example 1 (acid number=0.48 mg. KOH/g and magnesium content=11 ppm) was added, with stirring at 110° C., 1.65 g. of 3,4-epoxy cyclohexyl methyl-3,4-epoxy cyclohexyl carboxylate, "ERL 4221" brand (a bisepoxide product available from Union Carbide). After ninety minutes, the acid number of the resulting Bisphenol A bis(diphenyl phosphate) product, "BDP", was 0.017 mg. KOH/g.

EXAMPLE 7

Purification of Reaction Mixture

Step 2: To 1232 g. of crude BDP that was previously washed with oxalic acid and water as described in step 1 of Example 1 (acid number=0.48 mg. KOH/g and magnesium content=11 ppm) was added, with stirring at 130° C., 1.68 g. of 3,4-epoxy cyclohexyl methyl-3,4-epoxy cyclohexyl carboxylate, "ERL 4221" brand (already described earlier. After 45 minutes, the acid number of the resulting Bisphenol A bis(diphenyl phosphate) product, "BDP", was 0.019 mg. KOH/g.

EXAMPLE 8

Purification of Reaction Mixture

Step 2: To 600 g. of crude BDP that was previously washed with oxalic acid and water as described in step 1 of Example 1 (acid number=0.53 mg. KOH/g and magnesium content=13 ppm) was added, with stirring at 65° C., 0.63 g. of propylene oxide. After six hours, the acid number of the resulting Bisphenol A bis(diphenyl phosphate) product, "BDP", was 0.054 mg. KOH/g.

EXAMPLE 9

Purification of Reaction Mixture

Step 2: To 1000 g. of crude resorcinol bis(diphenyl phosphate), "RDP", that was previously washed with oxalic acid and water as described in step 1 of Example 1 (acid number=0.30 mg. KOH/g and magnesium content=6 ppm) was added, with stirring at 70° C., 5.0 g. of 3,4-epoxy cyclohexyl methyl-3,4-epoxy cyclohexyl carboxylate, "ERL 4221" brand. After three hours, the acid number of the resulting Resorcinol bis(diphenyl phosphate) product, "RDP", was 0.014 mg. KOH/g.

EXAMPLE 10

Effect of Water on Acid Reduction

In this Example, 250 g. of wet bisphenol A bis(diphenyl phosphate), "BDP", (no drying step after washing with oxalic acid and water; containing 4-5% water), having an acid number 0.19 mg. KOH/g., was treated with 0.1214 g. of "ERL 4221" bis epoxide at 65° C. for four hours, producing a product having an acid number of 0.15 mg. KOH/g.

COMPARATIVE EXAMPLE 1

Effect of Magnesium on Acid Reduction

Step 1: To 705.0 g. of water, which was heated to 90° C. with stirring, was added 614.7 g. of the reaction mixture from Example 1. The mixture was agitated for sixty minutes and was allowed to separate. The acid number of the oil was 1.1 mg. KOH/g. The oil layer was washed once more with water at 65° C. and was dried under vacuum to give 599.1 g. of product. After filtration of the oil, the magnesium content of this product was 160 ppm, and the acid number was 0.58 mg. KOH/g.

Step 2: To 507.4 g. of the oil from step 1 (acid number=0.58 mg. KOH/g) was added, with stirring at 110° C., 1.71 g. of 3,4-epoxy cyclohexyl methyl-3,4-epoxy cyclohexyl carboxylate, "ERL 4221" brand. After one hour, the acid number of the resulting bisphenol A bis(diphenyl phosphate) product, "BDP", was 0.238 mg. KOH/g. Addition of supplemental ERL 4221 bis epoxide at 110° C. for one hour did not decrease the acid number.

The described mode of operation is batch, but the method is not restricted to batch operation. It can as well be performed in a continuous mode.

The foregoing Examples should not be construed in a limiting fashion since they merely relate to certain preferred embodiments of the present invention. The scope of protection desired is set forth in the claims that follow.

We claim:

1. A process for purifying crude bisphenol A bis(diphenyl phosphate), said process consisting essentially of washing said crude bisphenol A bis(diphenyl phosphate) with an aqueous acidic chelating agent composition and then, optionally, with water, to provide a washed bisphenol A bis(diphenyl phosphate), drying the resulting washed bisphenol A bis(diphenyl phosphate), to provide a dried bisphenol A bis(diphenyl phosphate) and treating the dried bisphenol A bis(diphenyl phosphate) with an epoxy group containing acid scavenger.

2. A process according to claim 1 in which the epoxy group containing acid scavenger is 3,4-epoxy cyclohexyl methyl-3,4-epoxy cyclohexyl carboxylate.

3. A process according to claim 1 in which washing with the chelating agent composition takes place at a temperature of from about 40° C. to about 90° C.

4. A process according to claim 1 in which treatment with acid scavenger takes place at a temperature of from about 25° C. to about 200° C.

5. A process according to claim 1 in which the number of equivalents of epoxy group containing acid scavenger is equal to or greater than the number of equivalents of acid present in the crude bisphenol A bis(diphenyl phosphate) based on the acid number of the crude bisphenol A bis(diphenyl phosphate).

6. A process according to claim 1 in which the dried bisphenol A bis(diphenyl phosphate) is treated with the epoxy group containing compound at a temperature ranging from about 40° C. to about 200° C.

* * * * *